US011030742B2

(12) United States Patent
Knoplioch et al.

(10) Patent No.: US 11,030,742 B2
(45) Date of Patent: Jun. 8, 2021

(54) SYSTEMS AND METHODS TO FACILITATE REVIEW OF LIVER TUMOR CASES

(71) Applicant: GE Precision Healthcare LLC, Wauwatosa, WI (US)

(72) Inventors: Jerome Knoplioch, Buc (FR); Jean-Marc Treutenaere, Aix-en-Provence (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 26 days.

(21) Appl. No.: 16/369,326

(22) Filed: Mar. 29, 2019

(65) Prior Publication Data
US 2020/0311912 A1    Oct. 1, 2020

(51) Int. Cl.
*G06T 7/00* (2017.01)
*G06T 11/00* (2006.01)
(52) U.S. Cl.
CPC .......... *G06T 7/0012* (2013.01); *G06T 11/003* (2013.01); *G06T 2207/20036* (2013.01); *G06T 2207/20104* (2013.01); *G06T 2207/20182* (2013.01); *G06T 2207/30056* (2013.01); *G06T 2207/30096* (2013.01)
(58) Field of Classification Search
CPC ................ G06T 7/0012; G06T 11/003; G06T 2207/20182; G06T 2207/20036; G06T 2207/30056; G06T 2207/20104; G06T 2207/30096
See application file for complete search history.

(56) References Cited

U.S. PATENT DOCUMENTS

| 6,067,366 | A | * | 5/2000 | Simanovsky | ...... G06K 9/00771 345/424 |
| 6,584,216 | B1 | | 6/2003 | Nyul et al. | |
| 7,532,748 | B2 | * | 5/2009 | Lara-Montalvo | ........................... A61B 5/02007 378/21 |
| 7,787,673 | B2 | * | 8/2010 | Vaz | .......................... G06K 9/44 382/128 |
| 8,594,400 | B2 | * | 11/2013 | Darrow | ................ G01R 33/543 382/128 |

(Continued)

OTHER PUBLICATIONS

EP application 20165054.6 filed Mar. 23, 2020—extended Search Report dated Aug. 7, 2020, 13 pages.

(Continued)

*Primary Examiner* — Xuemei G Chen
(74) *Attorney, Agent, or Firm* — Hanley, Flight & Zimmerman

(57) ABSTRACT

Apparatus, systems, and methods to process an interior region of interest in an anatomy image via a user interface are disclosed. An example apparatus is to at least: process an image to reduce noise in the image; identify at least one of an organ of interest or a region of interest in the image; analyze values in at least one of the organ of interest or the region of interest; process the at least one of the organ of interest or the region of interest based on the analyzed values to provide a processed object in the at least one of the organ of interest or the region of interest; and display the processed object for interaction via an interface, the display to include exposing at least one of the organ of interest or the region of interest.

19 Claims, 5 Drawing Sheets

(56) References Cited

U.S. PATENT DOCUMENTS

| | | | | |
|---|---|---|---|---|
| 8,761,479 B2* | 6/2014 | Avinash | ............... | A61B 6/032 382/131 |
| 8,781,197 B2* | 7/2014 | Wang | ............... | G01R 33/54 382/131 |
| 2005/0041769 A1* | 2/2005 | Launay | ............... | A61B 6/541 378/4 |
| 2005/0074155 A1* | 4/2005 | Alyassin | ............... | G06T 15/08 382/131 |
| 2005/0249392 A1* | 11/2005 | Allain | ............... | G06K 9/342 382/128 |
| 2006/0242146 A1* | 10/2006 | Piacsek | ............... | G06T 7/64 |
| 2007/0081710 A1* | 4/2007 | Hong | ............... | G06K 9/38 382/128 |
| 2009/0096807 A1* | 4/2009 | Silverstein | ............... | G06T 11/001 345/593 |
| 2013/0004041 A1* | 1/2013 | Yang | ............... | G06T 11/003 382/131 |
| 2013/0116554 A1* | 5/2013 | Kaiser | ............... | A61B 6/40 600/425 |
| 2013/0198687 A1 | 8/2013 | Bird et al. | | |
| 2015/0078641 A1* | 3/2015 | Tan | ............... | G06T 7/12 382/131 |
| 2015/0190533 A1* | 7/2015 | Newton et al. | ........ | A61B 6/032 424/9.452 |
| 2016/0012613 A1* | 1/2016 | Okerlund | ............... | A61B 6/503 382/131 |
| 2016/0180525 A1* | 6/2016 | Reynolds | ............... | G06T 7/0016 382/131 |
| 2016/0292874 A1* | 10/2016 | Hsieh | ............... | G06T 11/008 |
| 2017/0086768 A1* | 3/2017 | Hefetz | ............... | A61B 6/461 |
| 2018/0314906 A1* | 11/2018 | Yang | ............... | G06K 9/44 |
| 2019/0012815 A1 | 1/2019 | Dhanantwari | | |
| 2019/0139223 A1* | 5/2019 | Nie | ............... | G06T 7/187 |
| 2020/0126236 A1* | 4/2020 | Rister | ............... | G06T 7/30 |
| 2021/0004956 A1* | 1/2021 | Book | ............... | G06T 11/008 |

OTHER PUBLICATIONS

William P. Shuman: "Iterative Reconstruction in CT: What Does It Do? How Can I Use It?", Image Wisely, Sep. 2016 (Sep. 2016), XP055719038, Retrieved from the Internet: URL:https://www.imagewisely.org/-/media/Image-Wisely/Files/CT/IW-Shuman-ASIR.pdf [retrieved on Jul. 29, 2020] ; 6 pages.

Xiuying Wang et al: "Automated liver segmentation for whole-body low-contrast CT images from PET-CT scanners", Proceedings of the 31st Annual International Conference of the IEEE Engineering in Medicine and Biology Society: Engineering the Future of Biomedicine, EMBC 2009, IEEE, Sep. 3, 2009 (Sep. 3, 2009), pp. 3565-3568, XP031880996, DOI: 10.1109/IEMBS.2009.5332410 ISBN: 978-1-4244-3296-7 ; 4 pages.

Nyul L G et al, "On standardizing the MR image intensity scale", Magnetic Resonance in Medicine, John Wiley & Sons, Inc, US, (1999), vol. 42, No. 6, doi:10.1002/(SICI)1522-2594 (1999)42:6<1072::AID-MRM11>3.0.CO,2-M, ISSN 0740-3194, 10 pages.

* cited by examiner

SYSTEMS AND METHODS TO FACILITATE REVIEW OF LIVER TUMOR CASES

FIELD OF THE DISCLOSURE

This disclosure relates generally to improved medical systems and, more particularly, to improved learning systems and methods for medical image processing.

BACKGROUND

A variety of economy, operational, technological, and administrative hurdles challenge healthcare facilities, such as hospitals, clinics, doctors' offices, imaging centers, teleradiology, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

In the medical field there exists many different types of medicals scans including X-ray, magnetic resonance imaging (MRI), ultrasound, computed tomography (CT), positron emission tomography (PET), etc. After a patient is scanned at the hospital, the resulting image can be displayed in a variety of ways. For example, an X-ray can be printed out on a film and shown to a radiologist to diagnose an injury or the film may be shown to a patient allowing for transparency in patient care. A physically printed film limits the viewer to a two-dimensional (2D) view of the scan. Alternatively, many exams can be displayed on a monitor, including a television, computer monitor, tablet, etc. A monitor can offer several advantages over a printed film for certain exams allowing rapid navigation between images. Digital images displayed on a monitor, depending on the type of exam, can offer the ability to zoom into certain areas of an exam as well as the ability to rotate the image for a different viewing angle. Although an image displayed on a digital monitor may provide dynamic points of viewing, this method of viewing can still be improved upon.

BRIEF SUMMARY

Certain examples provide apparatus, systems, and methods to process an interior region of interest in an anatomy image via a user interface.

Certain examples provide an apparatus including: at least one processor; and at least one computer readable storage medium including instructions. The instructions, when executed, cause the at least one processor to at least: process an image to reduce noise in the image; identify at least one of an organ of interest or a region of interest in the image; analyze values in at least one of the organ of interest or the region of interest; process the at least one of the organ of interest or the region of interest based on the analyzed values to provide a processed object in the at least one of the organ of interest or the region of interest; and display the processed object for interaction via an interface, the display to include exposing at least one of the organ of interest or the region of interest.

Certain examples provide at least one computer readable storage medium including instructions which, when executed, cause at least one processor to at least: process an image to reduce noise in the image; identify at least one of an organ of interest or a region of interest in the image; analyze values in at least one of the organ of interest or the region of interest; process the at least one of the organ of interest or the region of interest based on the analyzed values to provide a processed object in the at least one of the organ of interest or the region of interest; and display the processed object for interaction via an interface, the display to include exposing at least one of the organ of interest or the region of interest.

Certain examples provide a computer-implemented method including processing, by executing an instruction using at least one processor, an image to reduce noise in the image. The example method includes identifying, by executing an instruction using the at least one processor, at least one of an organ of interest or a region of interest in the image. The example method includes analyzing, by executing an instruction using the at least one processor, values in at least one of the organ of interest or the region of interest. The example method includes processing, by executing an instruction using the at least one processor, the at least one of the organ of interest or the region of interest based on the analyzed values to provide a processed object in the at least one of the organ of interest or the region of interest. The example method includes displaying, by executing an instruction using the at least one processor, the processed object for interaction via an interface, the display to include exposing at least one of the organ of interest or the region of interest.

Figure 1:
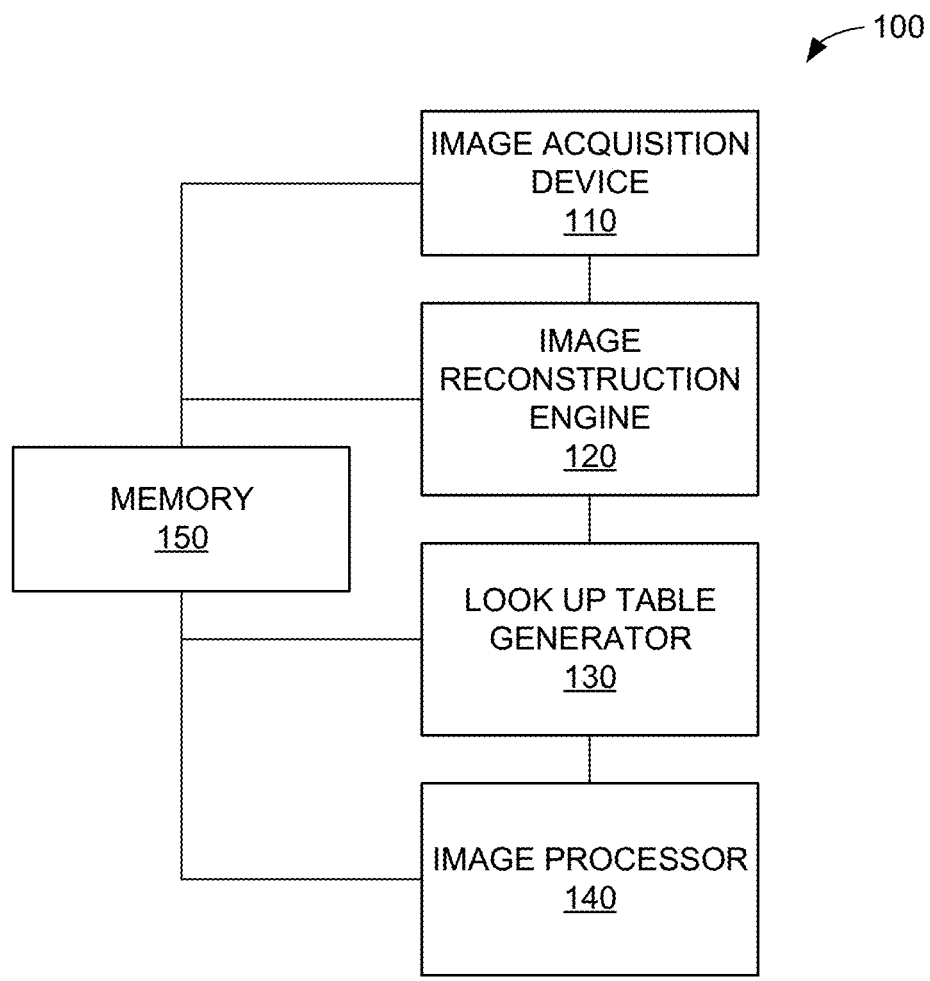
FIG. 1 illustrates an example image processing apparatus.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings. The figures are not scale. Wherever possible, the same reference numbers will be used throughout the drawings and accompanying written description to refer to the same or like parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment.

Most clinical decisions are derived from an analysis of a critical set or sets of interest from some data sources. In the radiology domain, this typically involves the analysis of regions of interest from medical image data. Medical image analysis is performed at the request of a referring physician for a specific purpose such as detection, assessment, progression of anatomical abnormalities (e.g., lesions, aneurysms, atrophies, etc.), etc. To analyze and/or otherwise process image data, images are reconstructed from the image data to be displayed, processed, stored, etc.

Image reconstruction refers to the generation of a 2D and/or 3D image from imaging data (e.g., light intensity values, etc.) obtained in a medical scan by an imaging device. For example, a 3D CT image volume can be reconstructed from a plurality of images obtained by the CT imaging device. The images are correlated through reconstruction to form the image volume.

Image reconstruction can include a filtered back projection reconstruction, which directly calculates an image in a single reconstruction step, or an iterative reconstruction, which begins with an assumption of the image, computes projections from that image, and iterates to update the image based on a comparison between computed projections and original projection data acquired by the image device. Such assumption and iteration, however, can introduce noise into the reconstructed image.

An example image reconstruction technique includes adaptive statistical iterative reconstruction (ASiR). Using ASiR, a pixel noise standard deviation can be reduced, along with a reduction in patient dosage to obtain the image data. ASiR processes raw image data and extracts noise using photon statistics and object modeling. Through iteration, ASiR extracts noise by modeling its root causes for each patient and application type.

Image reconstruction technologies, such as ASiR, can be used in image reviews, such as tumor reviews (e.g., liver tumor, etc.). For example, a tumor (e.g., liver tumor, etc.) review process can include processing image data to generate one or more images, displaying the one or more images, and generating a look-up table tailored to a tumor type (e.g., a liver and associated liver tumor, etc.) to be applied to enhance structures in the one or more images based on the tumor type.

For example, processing can include preprocessing and/or reconstructing one or more images with a technique to remove noise and irrelevant pattern information from the image(s). An example of such technique is ASiR reconstruction for CT images. Other relevant techniques include diffusion filters, guided filters, etc. In certain examples, machine learning (e.g., deep learning, other model-based methods, etc.) and/or other artificial intelligence can be used for image reconstruction and analysis by identifying patterns based on learned/observed historical data to develop models for reconstruction of an image from image data, analysis of the image to identify feature(s) of interest, etc. For example, an artificial intelligence (AI) model and its associated algorithm can be trained on a large number of images to reconstruct the CT images with better noise characteristics (e.g., noise reduction, etc.).

Resulting image(s) can be displayed with a display look up table that enhances structures inside an anatomy of interest, such as a liver parenchyma, etc. For example, a look up table can be generated based on centering a linear ramp on a Hounsfield value average inside the liver and adjusting its slope based on a standard deviation or a fixed value for CT images. Other example techniques involve using a non-linear lookup table to enhance the conspicuity of structures inside the parenchyma and/or other region of interest. While examples are described herein with respect to CT images, techniques are also applicable to adjust voxel/pixel values originating from other imaging modalities including MR, etc.

An enhanced or "optimal" look up table can be generated for an organ or other anatomy of interest (e.g., focusing on the liver to identify liver tumors, etc.). Look up table parameters can be learned based on a history of user settings, for example. Look up table parameters can be used to apply certain settings or functions to image data. Thus, the look up table can be used to enhance certain parts of an image and/or otherwise automatically process obtained image data.

For example, the look up table can be used to automatically apply window/level controls to an image. In medical imaging, a brightness/contrast control is referred to as a "window/level" control. Windowing, also known as grey-level mapping, contrast stretching, histogram modification, and/or contrast enhancement is a process in which a grayscale component of a CT image is manipulated to change an appearance of the image to highlight particular structure(s). This windowing adjustment can be facilitated using values in the look up table. A brightness of the image is adjusted via the window level, and a contrast of the image is adjusted via the window width, for example. The window width specifies a range of CT intensity values included in the image. A wider window width (e.g., 2000 Hounsfeld units, etc.) displays a wider range of CT values in an image than a narrower window width (e.g., 1000 Hounsfeld units, etc.) displays in the image. Thus, setting the window width for the image to 2000 Hounsfeld units adjusts a transition from dark to light structures within the image over a larger transition area than a narrower window width of 1000 Hounsfeld units, for example. As window width becomes wider, transitions between different attenuations in soft tissues become obscured, for example. As such, a wide window can be defined when looking at an area of greatly differing attenuation (e.g., in a lung image with air and tissue, etc.), but a narrow window can be defined when examining an area having soft tissue of similar attenuation, for example.

The window level, also referred to as the window center, defines a midpoint in a range of CT intensity values displayed for the image. Thus, when the window level is increased, the CT image is darker, and, when the window level is decreased, the CT image is brighter, for example.

Using window width (WW) and window level (WL), threshold(s) or transition(s) can be calculated to govern CT pixel intensity values. For example, CT values over an upper threshold can be displayed as white, and CT values under a lower threshold can be displayed as black. CT values in between the first and second thresholds can be displayed in greyscale, for example. The look up table can specify conversions from CT values to displayed intensity greyscale/color values, for example. Thus, the look up table can be constructed to map raw image data values to display pixel values, for example. Using values in the look up table, certain areas or objects in an image can be reduced in intensity or focus (e.g., whited out, muted, blacked out, etc.) and/or other areas/objects can be emphasized (e.g., through brighter color, sharper contrast, etc.) to focus attention and evaluation on a region/object of interest, for example. In certain examples, a characteristic curve and/or other function can be applied to image data as defined by a correlation between CT values and pixel display values defined in the look up table. Processing can be done quickly and efficiently to process the image (e.g., image contrast enhancement, brightness adjustment, gray value adjustment, gradation curve setting, etc.) by applying the look up table to acquired image data using a processor, for example.

In an example, a first action involves processing, such as using image-based filtering or adaptive iterative reconstruction, etc., to reduce noise inside the organ of interest. Then, a region inside the organ of interest is automatically extracted. In the case of the liver, the process includes removing voxels outside of the soft tissue range and applying a mathematical morphology closure filter to fill small holes created by vascular structures. A largest connected component is selected, and, inside the connected component, a slice with the largest number of pixels is selected. Slices within a given thickness around this largest slice are also selected. Then, the object imaged is eroded to select internal voxels. Within this region, mean and standard deviation values are to be computed. A display look up table can be generated by determining correlation or translation values between CT and pixel intensities as a linear ramp such as:

$$DisplayedValue=K(HUValue-mean+O)/(K.STD) \quad \text{(Equation 1),}$$

where O and K are values learned (e.g., averaged, etc.) from previous display sessions, and HUValue is a Hounsfield unit value. In certain examples, learned K and O values can be adjusted based on one or more environmental and/or lighting conditions such as whether or not the image was obtained in a dark room, etc. Thus, the pixel display value (DisplayedValue) correlates to the CT intensity value (HUValue) modified by historical observed values, associated mean (e.g., a mean of prior observed K and O values), and a standard deviation (STD) in prior K value, for example. Alternatively or in addition, lower and upper percentages of a histogram can be identified (e.g., black for values in the lower 1% of the histogram, white for values above 99% in the histogram, etc.) to adjust the pixel display value, for example.

A Hounsfield unit is a measure of a radiodensity of a substance. Hounsfield units (HU) are dimensionless units used in CT scanning to express CT numbers in a standardized and convenient form. Hounsfield units are obtained from a linear transformation of measured attenuation coefficients. This transformation is based on arbitrarily assigned densities of air and water, for example.

In certain examples, one or more algorithms can be applied to determine optimal or otherwise improved window level settings. Equation 1 provides one example, but other processes involving histogram equalization and/or other methods involving separating histograms from selected region into a number of classes and using the class number (from lowest HU to highest HU) to form the displayed value, etc., can be applied. Thus, certain examples can automatically set window level and/or other display values for a region of interest in an image to form an augmented and/or processed image. In certain examples, the augmented/processed image(s) can be diagnosed using computer-aided detection, such as using deep learning, etc., to identify a tumor, gauge tumor growth/shrinkage, etc., from the processed image data.

Thus, while identifying objects, such as liver tumors, etc., in an image is time-consuming, tedious and subject to misses (e.g., low sensitivity for less conspicuous tumors, etc.), certain examples provide improved image display and analysis to enable automatic and/or otherwise enhanced identification of the object in the image(s). Further, while high acquisition noise degrades image quality and makes tumors less visible in the image data, certain examples reduce such noise and improve reading confidence for low dose exams. Thus, image reading and analysis can be more sensitive and faster resulting in a higher sensitivity and diagnostic confidence, even at lower exposure doses to the patient.

FIG. 1 illustrates an example image processing apparatus 100 including an image acquisition device 110, an image reconstruction engine 120, a look up table generator 130, an image processor 140, and memory 150. The example image acquisition device 110 acquires image data from/representative of a patient. For example, the image acquisition device 110 obtains an image of the patient (e.g., a CT image, MR image, x-ray image, ultrasound image, etc.). Alternatively or in addition, the image acquisition device 110 receives and stores an image of the patient obtained by another device. Image data can be stored in memory 150 (e.g., a hard disk drive, flash memory, random access memory, other disk storage, other solid state storage, firmware, etc.).

The image reconstruction engine 120 processes the image data using image-based filtering, adaptive iterative reconstruction, AI model, etc., to reduce noise inside an organ/anatomy and/or other region of interest found in the image data. The organ/anatomy of interest can be specified in a primary exam record, a reason for exam notation, a DICOM image file header, an image and/or exam context, etc. In certain examples, a system, device, application, user, etc., can be prompted to specify and/or confirm the organ/anatomy of interest. Once the organ/anatomy of interest is identified and/or otherwise specified, noise can be reduced by one or more techniques including the AI model(s), image-based filtering, adaptive iterative reconstruction, etc. The image reconstruction engine 120 can perform two-dimensional (2D) image reconstruction and noise reduction, three-dimensional (3D) image reconstruction and noise reduction, etc. Reconstructed image(s) and associated data can be stored in memory 150.

The look up table generator 130 generates a look up table to be applied to the constructed and/or otherwise processed image data to adjust image pixel values to emphasize or highlight certain areas of the image (e.g., tumors, lesions, fractures, etc.). The range of pixel values produced during image reconstruction is larger than the range of values that can be displayed by a monitor or other display. Therefore, the look up table can be used to select a subset or range of values that is to be visualized. The range of values to be visualized corresponds to tissue/area of interest. The look up table and/or other function (e.g., a transfer function, a ramp or range between different image values, etc.) can be used to provide contrast/differentiation between image pixels, which translates into visual distinctions (e.g., clearer visual distinctions than uniform translation, etc.) between areas of an image on a display (e.g., in a radiology image reader/viewer and/or other display, etc.). The look up table can be stored in memory 150 to be applied by one or more processes/processors, for example.

For example, the look up table generator 130 executes Equation 1 to populate the look up table with values to translate or transform CT values to image pixel/voxel values, transform first image pixel values to second image pixel values (e.g., to emphasize or deemphasize certain image area(s), certain object(s), certain type(s) of tissue, etc.), etc. The generated look up table can be stored in memory 150, applied (e.g., by the image reconstruction engine, the image processor 140, etc.) to image data, modified based on user input, prior/historical observations/feedback/results, AI model output, etc.

For example, a look up table can be generated to provide a "default" window level and width for an abdomen in an image (Width: 440, Level: 40). The example look up table then specifies that values below 40−220 HU are black, and values above 40+220 are white, with values in between assigned grayscale values. These values can vary based on choice of injection to help ensure that lesions are not missed because the contrast is not sharp enough or the image is saturated, for example.

Thus, the look up table generator 130 can generate a look up table and/or other processing data structure to enhance particular structures in an anatomy of interest (e.g., inside the liver parenchyma, etc.), for example. For example, the generated look up table can center a linear ramp on a Hounsfield value average inside the organ/anatomy of interest (e.g., liver, lung, heart, brain, etc.) and adjust a slope of the ramp based on standard deviation and/or a fixed value. Another example uses a non-linear lookup table to the same effect of enhancing the conspicuity of structures inside the organ (e.g., liver parenchyma, etc.).

The image processor 140 processes the image(s) (e.g., the reconstructed image(s), etc.) to detect an anatomy or region of interest and focus on that anatomy/region of interest. For example, the image processor 140 can process a reconstructed 3D image volume to remove, erode, or "peel back" outer voxels of the image volume to uncover or expose a region of interest. In certain examples, a region of interest can be inside an identified organ. The organ can be isolated, and then outer voxels of the organ can be removed to expose a region of interest inside the organ. Thus, for example, a liver can be isolated in an image, and then outer voxels of the liver can be eroded (e.g., using the lookup table to cancel voxel values, using a filter to remove pixels/voxels, via image segmentation, etc.) to expose a region of interest inside the organ of interest.

For example, a region inside an organ of interest can be automatically extracted by the image processor 140 by removing voxels outside of the soft tissue range of the organ (e.g., liver, etc.). A mathematical morphology closure filter can be applied by the processor 140 to fill small holes created by vascular structures in the organ. The image processor 140 can select largest connected component in the organ/anatomy, and, inside the connected component, an obtained image slice with a largest number of pixels is selected. Once the image processor 140 has the selected slice, additional slices within a given thickness or range around this largest slice are also selected by the processor 140. The organ/anatomy is then eroded to remove outer voxels outside the slices and select internal voxels for further processing. Within this region, the image processor 140 computes mean and standard deviation values for image voxel data. The display look up table (LUT) is generated by the generator 130 as a linear ramp such as according to Equation 1, for example. Application of the LUT to the exposed region image values can be used to identify a liver tumor, lesion, etc., for example. Alternatively or in addition, other deep learning, machine learning, and/or model-based approaches can be employed to identify and extract the region of interest.

While several algorithms can be applied to determine optimal window level settings for the look up table, Equation 1 provides an effective contrast. In certain examples, histogram equalization and/or other methods involving separation of a histogram from the selected region into a number of classes and using the class number (e.g., from lowest HU to highest HU) can be used as a reference for pixel/voxel value distribution inside "normal" tissues so that "abnormal" tissues stand out in the display. After noise reduction, the voxel value range obtained can be narrow and may include a single class of voxels, for example.

Thus, the image processor 140 can drive a modified display of the image data to highlight one or more areas of the 2D and/or 3D image based on the algorithm applied by the look up table and/or associated ramp, etc. A visual distinction is applied to image data to alter the display of the image and emphasize elements such as lesions, tumors, fractures, and/or other abnormality(-ies), for example. In certain examples, a user can interact with the object(s) of interest and/or other aspect of the image display on a screen via a graphical user interface, etc.

Figure 2:
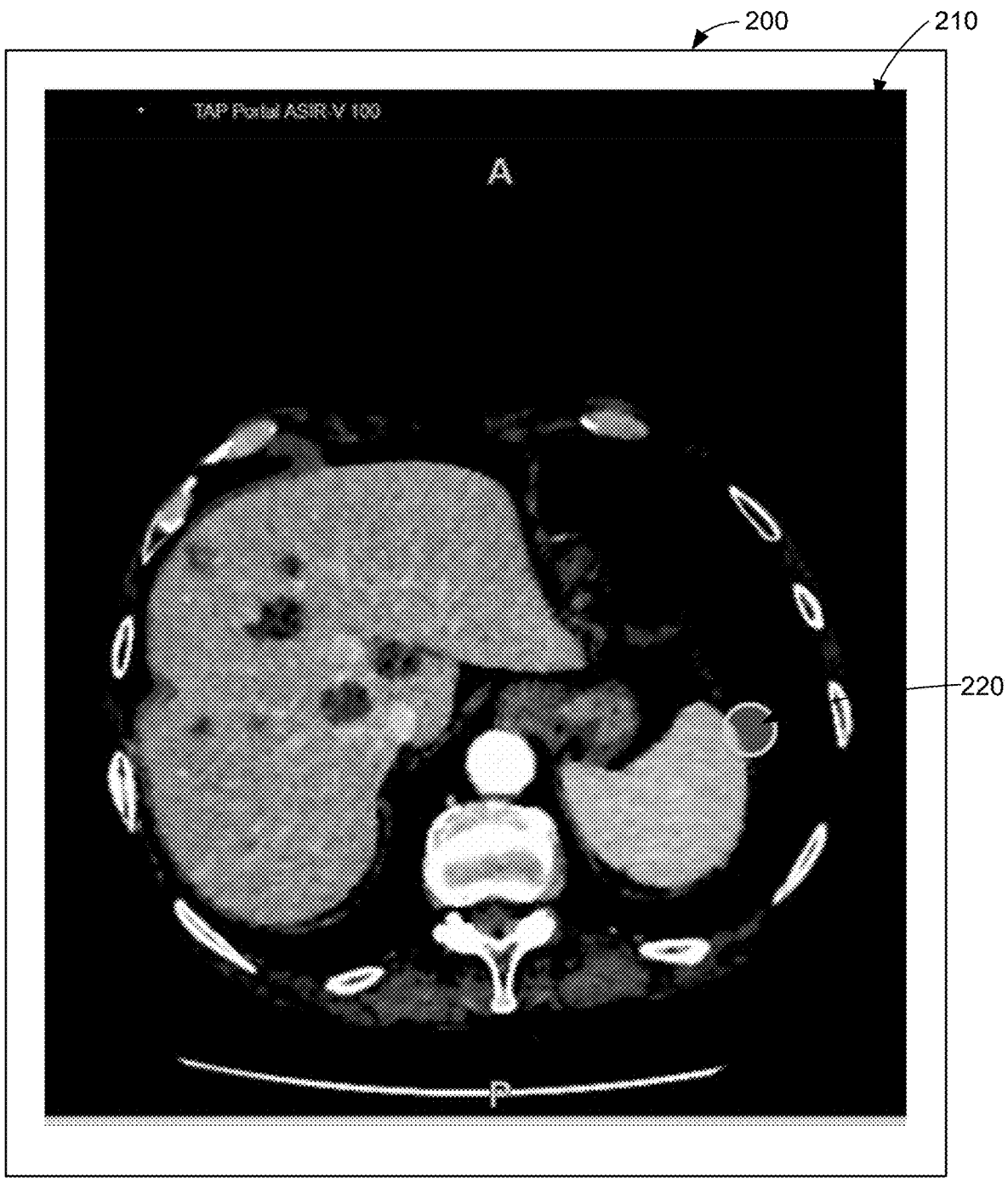
FIG. 2 illustrates an example interface including an image and object of interest processed and displayed using the example apparatus of FIG. 1.

FIG. 2 illustrates an example user interface 200 to display an example brain CT image 210 processed by the system 100 to identify a tumor 220 in the example image 210. As shown in the example of FIG. 2, the image processor 140 can highlight (e.g., by encircling, putting in a box, shading, etc.) the identified object (e.g., tumor, lesion, etc.) 220 in the image 210.

While example implementations are illustrated in conjunction with FIGS. 1-2, elements, processes and/or devices illustrated in conjunction with FIGS. 1-2 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 3:
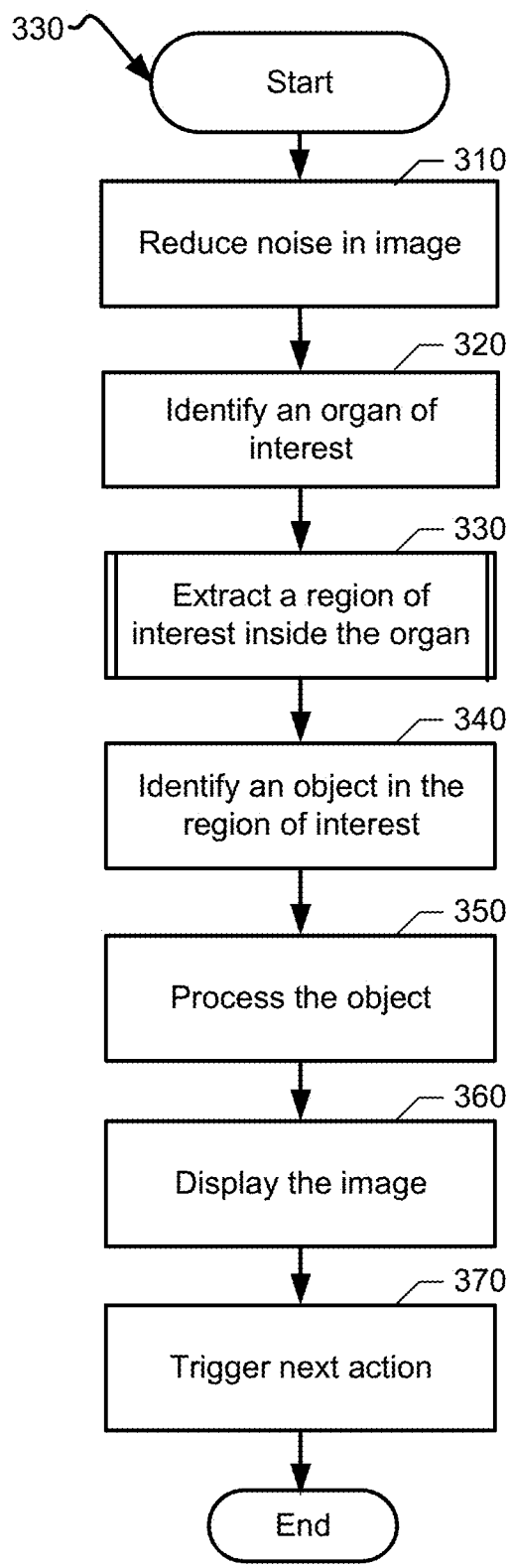
FIGS. 3-4 illustrate flow diagrams of example methods of image processing and display using the apparatus of FIGS. 1-2.
Figure 4:
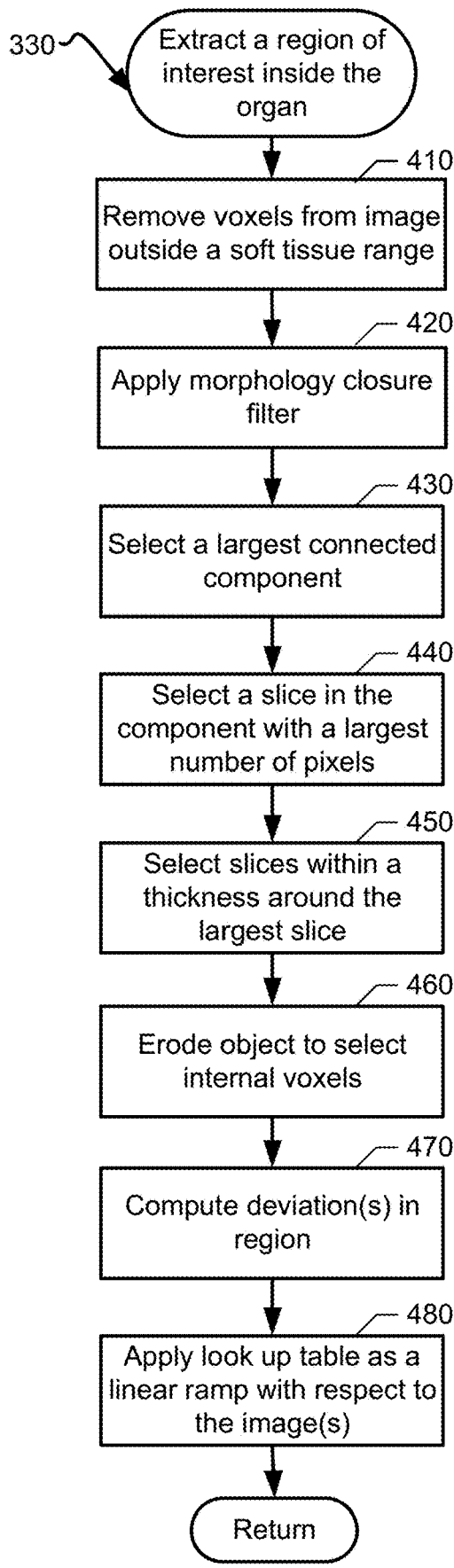

A flowchart representative of example machine readable instructions for implementing components disclosed and described herein are shown in conjunction with at least FIGS. 3-4. In the examples, the machine readable instructions include a program for execution by a processor such as the processor 512 shown in the example processor platform 500 discussed below in connection with FIG. 5. The program may be embodied in machine readable instructions stored on a tangible computer readable storage medium such as a CD-ROM, a floppy disk, a hard drive, a digital versatile disk (DVD), a Blu-ray disk, or a memory associated with the processor 512, but the entire program and/or parts thereof could alternatively be executed by a device other than the processor 512 and/or embodied in firmware or dedicated hardware. Further, although the example program is described with reference to the flowchart illustrated in conjunction with at least FIGS. 3-4, many other methods of implementing the components disclosed and described herein may alternatively be used. For example, the order of execution of the blocks may be changed, and/or some of the blocks described may be changed, eliminated, or combined. Although the flowcharts of at least FIGS. 3-4 depicts example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) of at least FIGS. 3-4 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of at least FIGS. 3-4 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As shown in the example method 300 depicted in FIG. 3, image data is processed to identify and highlight/emphasize one or more objects in a region of interest in the image. At block 310, the image is processed (e.g., "cleaned up", etc.) to reduce noise in the image. For example, reconstruction (e.g., ASIR reconstruction, etc.), filtering (e.g., diffusion filtering, guided filtering, etc.), etc., can be applied to the image data to remove noise and irrelevant pattern(s) from the image (e.g., one or more 2D and/or 3D images).

At block 320, an organ of interest is identified and/or otherwise determined in the cleaned image. For example, a reason for exam, header information, imaging device configuration information, computer-aided detection (e.g., via machine learning, deep learning, other AI, etc.), etc., can identify an organ of interest (e.g., brain, heart, lungs, kidneys, etc.) in the image.

At block 330, a region of interest is extracted inside the organ of interest. For example, pixels and/or voxels can be removed form the outside of the organ to expose internal pixels/voxels forming the region of interest. Imperfections can be smoothed/filled to isolate the region for further processing.

At block 340, an object is identified in the extracted region of interest. For example, a look up table, ramp, and/or other transformation function can be applied to the pixel/voxel data in the region of interest to analyze objects (e.g., tissue, bone, tumor, lesion, fracture, etc.) in the exposed region of interest. For example, applying look up table values to different CT intensities in the region of interest causes the object (e.g., a tumor, etc.) to stand out from the rest of the region image data (e.g., because it displays as brighter, darker, and/or otherwise different from surrounding tissue.

At block 350, the object is processed. For example, the identified object can be processed using computer added diagnosis (CAD), radiology reading, etc., to identify a characteristic of the object such as a type of the object (e.g., tumor, lesion, fracture, etc.), a shape of the object, a size of the object, a change in the object (e.g., if comparing images to see tumor growth, etc.), etc. Thus, at blocks 340-350, values (e.g., image data values, pixel/voxel display values, etc.) are analyzed to identify the object and process the object for display and interaction.

At block 360, the modified image is displayed. For example, the modified image can be displayed on a tablet computer (such as shown in the example of FIG. 2), on a laptop computer, on a computer monitor, on a smartphone display, etc. As shown in the example of FIG. 2, the image 210 can be shown via the interface 200 with the object 220 highlighted in the image 210, etc.

At block 370, a next action is triggered. For example, a report can be generated including and/or based on the image, a finding/annotation associated with the object, etc. The image and/or associated report can be stored in an electronic medical record (EMR) system, etc. Identification of the object in the image can trigger an exam scheduling, a prescription, and/or other follow up action, for example. An action of a user with respect to the image 210 and/or object 220 via the interface 200 can trigger a next action, for example.

FIG. 4 illustrates an example implementation of extracting a region of interest inside an organ (block 330 of the example of FIG. 3). This example is provided for purposes of illustration only, and other methods including deep learning, machine learning, other model-based analyses, etc., can be employed to extract the region of interest. In the example of FIG. 4, at block 410, voxels from the image are removed outside of a soft tissue range. For example, a soft tissue range is defined around the organ of interest, and voxels in the image volume outside the soft tissue range are removed, erased, and/or otherwise deleted from a copy of the image volume being processed.

At block 420, a filter is applied to smooth the resulting sub-image. For example, a mathematical morphology closure filter is applied to the sub-image to fill small holes in the organ interior that are created by vascular structures (e.g., blood vessels).

At block 430, a largest connected component in the sub-image is selected. For example, connections between elements in the sub-image are analyzed by the image processor 140 to identify the largest connected component in the sub-image. In some examples, a user can select the largest connected component.

At block 440, a slice within the largest connected component is selected. For example, the selected slice has a largest number of pixels in the component. For example, the image processor 140 can process the component to identify the 2D slice from the component volume having the most pixels. At block 450, slices within a certain thickness around this largest slice are selected. For example, slices within an inch of the selected slice, slices within a centimeter of the selected slice, slices within a millimeter of the selected slice, etc., can also be selected. The set of selected slices form a volume, such as the organ of interest, for example.

At block 460, the selected slices are further processed to erode the set of selected slices to expose internal voxels in the volume. For example, a layer of voxels forming an outer portion of the volume defined by the set of selected slices can be erased, deleted, and/or otherwise removed to expose the next layer of voxels underneath. Thus, an interior region of interest of the organ of interest is exposed.

At block 470, deviations are computed for the region of interest. For example, a mean, standard deviation, etc., of CT intensity values within the region of interest are computed. At block 480, a display look up table and/or other transform is determined to modify displayed pixel/voxel values within the region of interest. For example, an LUT, such as specified by the ramp function of Equation 1, is applied to modify display values of voxels in the region of interest to accentuate/emphasize part of the region, such as a tumor, lesion, etc., for display. The values of the LUT can be influenced by prior display values (e.g., automatically processed values, feedback from manual user adjustment, etc.), for example. Thus, improved window level settings can be set using AI, learned from previous display sessions, averaged from prior configurations, etc., to display an image with an object of interest highlighted/emphasized/identified for further processing and review, for example.

Figure 5:
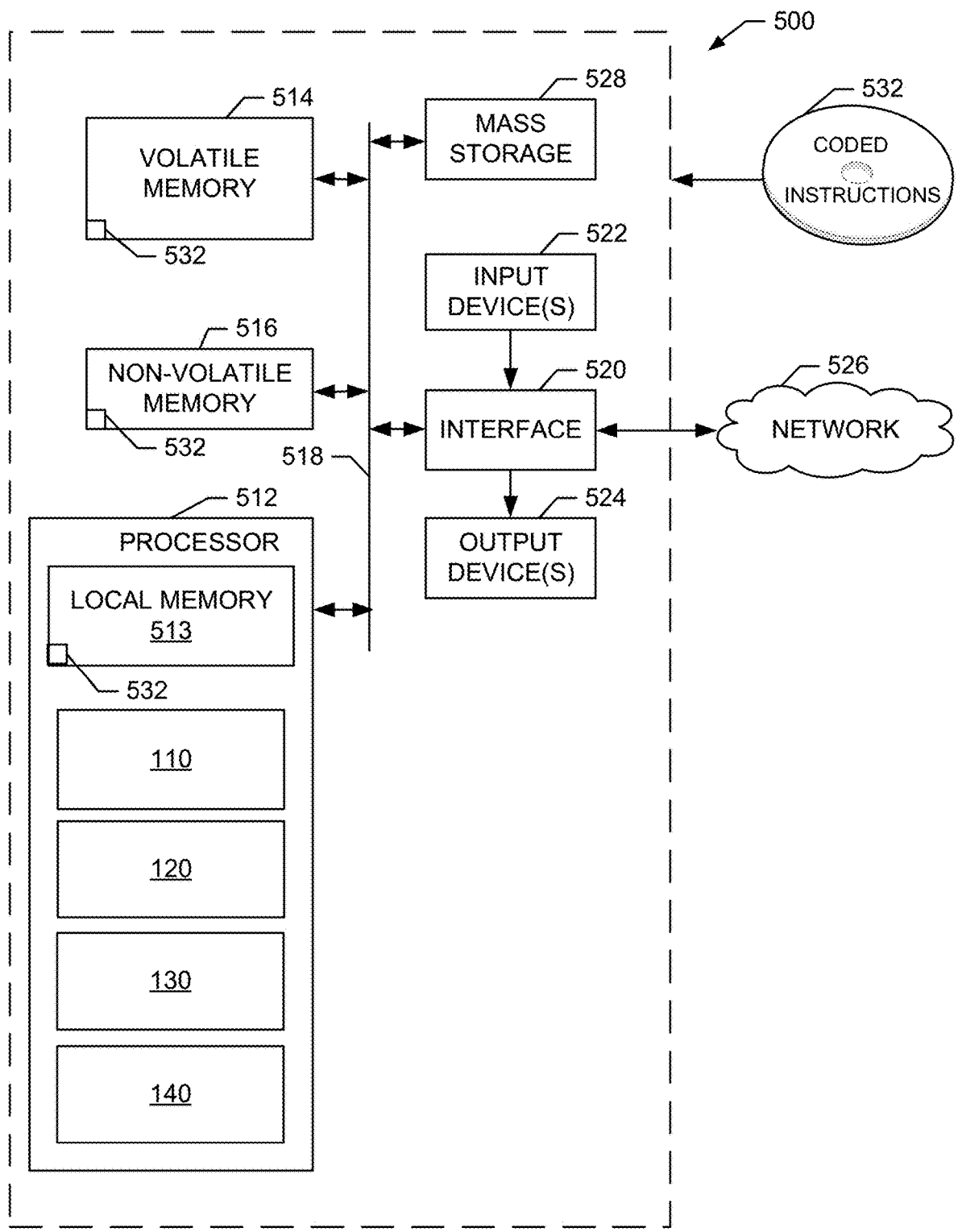
FIG. 5 is a block diagram of a processor platform structured to execute the example machine readable instructions to implement components disclosed and described herein.

FIG. 5 is a block diagram of an example processor platform 500 structured to executing the instructions of at least FIGS. 3-4 to implement the example components disclosed and described herein. The processor platform 500 can be, for example, a server, a personal computer, a mobile device (e.g., a cell phone, a smart phone, a tablet such as an iPad™), a personal digital assistant (PDA), an Internet appliance, or any other type of computing device.

The processor platform 500 of the illustrated example includes a processor 512. The processor 512 of the illustrated example is hardware. For example, the processor 512 can be implemented by integrated circuits, logic circuits, microprocessors or controllers from any desired family or manufacturer.

The processor 512 of the illustrated example includes a local memory 513 (e.g., a cache and/or memory implementing the example memory 150 and/or other memory). The example processor 512 of FIG. 5 executes the instructions of at least FIGS. 3-4 to implement the systems, infrastructure, displays, and associated methods of FIGS. 1-4 such as the example image acquisition device 110, the example image reconstruction engine 120, the example look up table generator 130, the example image processor 140, etc. The processor 512 of the illustrated example is in communication with a main memory (e.g., implementing the memory 150, etc.) including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a clock controller.

The processor platform 500 of the illustrated example also includes an interface circuit 520. The interface circuit 520 may be implemented by any type of interface standard, such as an Ethernet interface, a universal serial bus (USB), and/or a PCI express interface.

In the illustrated example, one or more input devices 522 are connected to the interface circuit 520. The input device(s) 522 permit(s) a user to enter data and commands into the processor 512. The input device(s) can be implemented by, for example, a sensor, a microphone, a camera (still or video, RGB or depth, etc.), a keyboard, a button, a mouse, a touchscreen, a track-pad, a trackball, isopoint and/or a voice recognition system.

One or more output devices 524 are also connected to the interface circuit 520 of the illustrated example. The output devices 524 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 520 of the illustrated example, thus, typically includes a graphics driver card, a graphics driver chip or a graphics driver processor.

The interface circuit 520 of the illustrated example also includes a communication device such as a transmitter, a receiver, a transceiver, a modem and/or network interface card to facilitate exchange of data with external machines (e.g., computing devices of any kind) via a network 526 (e.g., an Ethernet connection, a digital subscriber line (DSL), a telephone line, coaxial cable, a cellular telephone system, etc.).

The processor platform 500 of the illustrated example also includes one or more mass storage devices 528 for storing software and/or data. Examples of such mass storage devices 528 include floppy disk drives, hard drive disks, compact disk drives, Blu-ray disk drives, RAID systems, and digital versatile disk (DVD) drives.

The coded instructions 532 of FIG. 5 may be stored in the mass storage device 528, in the volatile memory 514, in the non-volatile memory 516, and/or on a removable tangible computer readable storage medium such as a CD or DVD.

From the foregoing, it will be appreciated that the above disclosed methods, apparatus, and articles of manufacture have been disclosed to improve image processing by automatically evaluating an image to determine an organ of interest and a region of interest within the organ. Certain examples further improve image processing by automatically eroding an exterior of the image of the organ to expose the region of interest. Certain examples even further improve image processing by modifying display values of the exposed region of interest to highlight and/or otherwise identify one or more objects in the exposed region of interest.

Certain examples improve radiology review interface technology and capabilities by providing a new and different process to render, display, and interact with image data. Certain examples improve an image processor to be more adaptive and accurate in image processing and user interface generation, manipulation, and tracking. Certain examples drive improvements in other technology areas such as computer-aided detection and/or diagnosis of image data, deep learning network model generation, etc.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
   at least one processor; and
   at least one computer readable storage medium including instructions which, when executed, cause the at least one processor to at least:
   process an image to reduce noise in the image;
   identify at least one of an organ of interest or a region of interest in the image;
   analyze values in at least one of the organ of interest or the region of interest;
   process the at least one of the organ of interest or the region of interest based on the analyzed values to provide a processed object in the at least one of the organ of interest or the region of interest; and
   display the processed object for interaction via an interface, the display to include exposing at least one of the organ of interest or the region of interest by at least:
   removing voxels from the image outside a soft tissue range to produce a modified image;
   applying a morphology closure filter to the modified image;
   selecting a largest connected component in the modified image;
   selecting a first slice in the largest connecting component having a largest number of pixels in the largest connected component;
   selecting a plurality of second slices within a thickness of the first slice to form an object;
   eroding the object to select internal voxels inside the object to expose the region of interest;
   computing deviation in the region of interest; and
   applying a look up table to display values of the region of interest.

2. The apparatus of claim 1, wherein the object in the exposed region of interest is to be processed using the look up table of display values associated with image data values.

3. The apparatus of claim 2, wherein the display values are to be determined using Displayed Value=K(HUValue−mean+O)/(K.STD),
   wherein K and O are prior values from previous display sessions, HUValue is a Hounsfield unit value, mean is a mean of prior values K and O, and K.STD is standard deviation in prior K value.

4. The apparatus of claim 1, wherein the object in the exposed region of interest is to be processed using a linear ramp function converting image data values to display values.

5. The apparatus of claim 1, wherein the image is to be processed to reduce noise in the image using adaptive statistical iterative reconstruction.

6. The apparatus of claim 1, wherein the organ is a liver and wherein the object is a liver tumor.

7. At least one computer readable storage medium including comprising instructions which, when executed, cause at least one processor to at least:
   process an image to reduce noise in the image;
   identify at least one of an organ of interest or a region of interest in the image;
   analyze values in at least one of the organ of interest or the region of interest;
   process the at least one of the organ of interest or the region of interest based on the analyzed values to provide a processed object in the at least one of the organ of interest or the region of interest; and
   display the processed object for interaction via an interface, the display to include exposing at least one of the organ of interest or the region of interest by at least:
   removing voxels from the image outside a soft tissue range to produce a modified image;
   applying a morphology closure filter to the modified image;
   selecting a largest connected component in the modified image;
   selecting a first slice in the largest connecting component having a largest number of pixels in the largest connected component;
   selecting a plurality of second slices within a thickness of the first slice to form an object;
   eroding the object to select internal voxels inside the object to expose the region of interest;
   computing deviation in the region of interest; and
   applying a look up table to display values of the region of interest.

8. The at least one computer readable storage medium of claim 7, wherein the object in the exposed region of interest is to be processed using the look up table of display values associated with image data values.

9. The at least one computer readable storage medium of claim 8, wherein the display values are to be determined using Displayed Value=K(HUValue−mean+O)/(K.STD),
   wherein K and O are prior values from previous display sessions, HUValue is a Hounsfield unit value, mean is a mean of prior values K and O, and K.STD is standard deviation in prior K value.

10. The at least one computer readable storage medium of claim 7, wherein the object in the exposed region of interest is to be processed using a linear ramp function converting image data values to display values.

11. The at least one computer readable storage medium of claim 7, wherein the image is to be processed to reduce noise in the image using adaptive statistical iterative reconstruction.

12. The at least one computer readable storage medium of claim 7, wherein the organ is a liver and wherein the object is a liver tumor.

13. A computer-implemented method comprising:
    processing, by executing an instruction using at least one processor, an image to reduce noise in the image;
    identifying, by executing an instruction using the at least one processor, at least one of an organ of interest or a region of interest in the image;
    analyzing, by executing an instruction using the at least one processor, values in at least one of the organ of interest or the region of interest;
    processing, by executing an instruction using the at least one processor, the at least one of the organ of interest or the region of interest based on the analyzed values to provide a processed object in the at least one of the organ of interest or the region of interest; and
    displaying, by executing an instruction using the at least one processor, the processed object for interaction via an interface, the display to include exposing at least one of the organ of interest or the region of interest by at least:
    removing voxels from the image outside a soft tissue range to produce a modified image;
    applying a morphology closure filter to the modified image;

selecting a largest connected component in the modified image;

selecting a first slice in the largest connecting component having a largest number of pixels in the largest connected component;

selecting a plurality of second slices within a thickness of the first slice to form an object;

eroding the object to select internal voxels inside the object to expose the region of interest;

computing deviation in the region of interest; and applying a look up table to display values of the region of interest.

14. The method of claim 13, wherein the object in the exposed region of interest is to be processed using the look up table of display values associated with image data values.

15. The method of claim 14, wherein the display values are to be determined using Displayed Value=K(HUValue−mean+O)/(K.STD), wherein K and O are prior values from previous display sessions, HUValue is a Hounsfield unit value, mean is a mean of prior values K and O, and K.STD is standard deviation in prior K value.

16. The method of claim 13, wherein the object in the exposed region of interest is to be processed using a linear ramp function converting image data values to display values.

17. The method of claim 13, wherein the image is to be processed to reduce noise in the image using adaptive statistical iterative reconstruction.

18. An apparatus comprising:

at least one processor; and at least one computer readable storage medium including instructions which, when executed, cause the at least one processor to at least:

process an image to reduce noise in the image;

identify at least one of an organ of interest or a region of interest in the image;

analyze values in at least one of the organ of interest or the region of interest;

process the at least one of the organ of interest or the region of interest based on the analyzed values to provide a processed object in the at least one of the organ of interest or the region of interest; and display the processed object for interaction via an interface, the display to include exposing at least one of the organ of interest or the region of interest by removing outer voxels of the image to expose the at least one of the organ of interest or the region of interest inside the image, wherein the object in the exposed region of interest is to be processed using a look up table of display values associated with image data values, the display values determined using Displayed Value=K(HUValue−mean+O)/(K.STD), wherein K and O are prior values from previous display sessions, HUValue is a Hounsfield unit value, mean is a mean of prior values K and O, and K.STD is standard deviation in prior K value.

19. At least one computer readable storage medium comprising instructions which, when executed, cause at least one processor to at least:

process an image to reduce noise in the image;

identify at least one of an organ of interest or a region of interest in the image;

analyze values in at least one of the organ of interest or the region of interest;

process the at least one of the organ of interest or the region of interest based on the analyzed values to provide a processed object in the at least one of the organ of interest or the region of interest; and display the processed object for interaction via an interface, the display to include exposing at least one of the organ of interest or the region of interest by removing outer voxels of the image to expose the at least one of the organ of interest or the region of interest inside the image, wherein the object in the exposed region of interest is to be processed using a look up table of display values associated with image data values, the display values determined using Displayed Value=K(HUValue−mean+O)/(K.STD), wherein K and O are prior values from previous display sessions, HUValue is a Hounsfield unit value, mean is a mean of prior values K and O, and K.STD is standard deviation in prior K value.

* * * * *